(12) United States Patent
Thomas et al.

(10) Patent No.: US 9,913,470 B2
(45) Date of Patent: Mar. 13, 2018

(54) SURFACE STERILISATION BY MISTING WITH A BIOFLAVANOID SOLUTION

(75) Inventors: Howard Thomas, Cambridgeshire (GB); Ian Ripley, Middlesbrough (GB)

(73) Assignee: CITROX BIOSCIENCES LIMITED, Cambridgeshire (GB)

( * ) Notice: Subject to any disclaimer, the term of this patent is extended or adjusted under 35 U.S.C. 154(b) by 0 days.

(21) Appl. No.: 13/147,949

(22) PCT Filed: Feb. 4, 2010

(86) PCT No.: PCT/GB2010/050180
§ 371 (c)(1),
(2), (4) Date: Aug. 4, 2011

(87) PCT Pub. No.: WO2010/089600
PCT Pub. Date: Aug. 12, 2010

(65) Prior Publication Data
US 2011/0294750 A1    Dec. 1, 2011

(30) Foreign Application Priority Data
Feb. 5, 2009 (GB) .................................. 0901901.9

(51) Int. Cl.
| | | |
|---|---|---|
| A01N 43/16 | (2006.01) |
| A01N 43/26 | (2006.01) |
| A01N 43/32 | (2006.01) |
| A23L 3/3472 | (2006.01) |
| A23L 3/3499 | (2006.01) |
| A23L 3/3544 | (2006.01) |
| A23L 3/3562 | (2006.01) |
| A01N 65/08 | (2009.01) |
| A01N 65/36 | (2009.01) |

(52) U.S. Cl.
CPC ............ *A01N 43/16* (2013.01); *A01N 43/26* (2013.01); *A01N 43/32* (2013.01); *A01N 65/08* (2013.01); *A01N 65/36* (2013.01); *A23L 3/3472* (2013.01); *A23L 3/3499* (2013.01); *A23L 3/3544* (2013.01); *A23L 3/3562* (2013.01)

(58) Field of Classification Search
CPC ........ A01N 43/16; A01N 65/36; A01N 65/08; C07H 17/04
USPC ........................... 514/27, 25, 456; 536/8, 4.1
See application file for complete search history.

(56) References Cited

U.S. PATENT DOCUMENTS

| | | | |
|---|---|---|---|
| 6,749,875 B2 * | 6/2004 | Selleck ..................... | A01N 3/02 426/270 |
| 2005/0123528 A1 * | 6/2005 | Gorton ..................... | A23B 4/22 424/94.1 |
| 2008/0226485 A1 | 9/2008 | Park et al. | |
| 2008/0226495 A1 * | 9/2008 | Sparks ........................... | 422/20 |
| 2009/0019563 A1 * | 1/2009 | Noro ..................... | A01H 5/0875 800/260 |

FOREIGN PATENT DOCUMENTS

| | | | |
|---|---|---|---|
| DE | 10234768 | 2/2004 | |
| EP | 0861662 | 9/1998 | |
| GB | 2450536 A | 12/2008 | |
| WO | WO-9966961 A1 * | 12/1999 | ............... A61L 2/22 |
| WO | 2004/091569 | 10/2004 | |
| WO | 2007/125100 | 11/2007 | |
| WO | 2008009956 A1 | 1/2008 | |
| WO | 2008009958 A1 | 1/2008 | |
| WO | 2009/106889 | 9/2009 | |

OTHER PUBLICATIONS

Peterson et al.; Journal of Food Composition and Analysis 19 (2006) S66-S73.*
Donnelly, T. et al "An experimental study on micron-scale droplet . . . " Phys. Fluids, vol. 16, No. 8, pp. 2843-2851. (Year: 2004).*
Search Report for corresponding British Application No. GB0901901.9, dated Jul. 23, 2010.
Office Action for corresponding European Application No. 10702905.0-2103 dated Jun. 11, 2012.
GDM Technologies Pty Ltd., Material Safety Data Sheet, Citrofresh Hospital Grade Disinfectant Concentrate, Jan. 15, 2008, p. 3PP.
GDM Technologies Pty Ltd., Citrofresh Internet Citation, Jul. 18, 2008.
GDM Technologies Pty Ltd., Material Safety Data Sheet, Croplife, Jan. 15, 2008, p. 3PP.
GDM Technologies Pty Ltd., Citrofresh Croplife (Plant Nutrient Synergist), Jul. 19, 2008.
GDM Technologies Pty Ltd., Material Safety Data Sheet, Citrofesh Concentrate, Jan. 15, 2008, p. 3PP.
International Search Report corresponding to PCT/GB2010/050180.

* cited by examiner

*Primary Examiner* — Leigh C Maier
(74) *Attorney, Agent, or Firm* — McCarter & English, LLP; Steven G. Davis; Wei Song

(57) ABSTRACT

There is described a method of sterilizing surfaces using flavonoids, for example mixtures containing inter alia naringin and neohesperidin, by misting.

11 Claims, No Drawings

SURFACE STERILISATION BY MISTING WITH A BIOFLAVANOID SOLUTION

CROSS REFERENCE TO RELATED APPLCIATIONS

This national phase application claims the benefit under 35 U.S.C. §371 of International Application No. PCT/GB2010/050180 filed on Feb. 4, 2010, entitled SURFACE STERILISATION BY MISTING WITH A BIOFLAVANOID SOLUTON, which in turn takes its priority from British Application No.GB0901901.9 filed on Feb. 5, 2009, and all of whose entire disclosures are incorporated by reference herein.

FIELD OF THE INVENTION

The present application relates to the sterilisation of surfaces by misting. More specifically this present application relates to the use of compositions containing certain flavonoids for sterilisation of surfaces, including those present in hospitals, ambulances and kitchens, by misting.

BACKGROUND OF THE INVENTION

Applications numbers PCT/GB2007/002756 and PCT/GB2007/002758, disclose compositions comprising certain flavonoids for use in oral and topical applications. It has now been found that surfaces may be sterilised by misting using compositions which contain some or similar flavonoids.

SUMMARY OF THE INVENTION

Accordingly the present invention provides a method of sterilising surfaces by misting which employs a compound of the Formula (I):

(I)

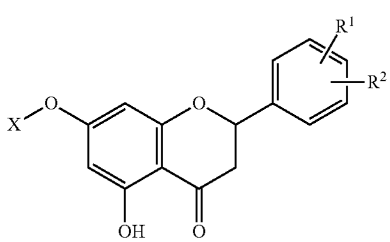

wherein $R^1$ is hydroxyl or methoxyl and $R^2$ is hydrogen, hydroxyl or methoxyl and X is hydrogen or a saccharide.

Aptly $R^2$ is hydrogen and $R^1$ is in the 3- or 4-position. Alternatively, aptly $R^2$ is 3-hydroxy and $R^1$ is 4-methoxyl.

Suitably X in a compound of the Formula (I) is H.

Suitably X in a compound of Formula (I) is a saccharide.

Favourably X is a disaccharide.

Suitable disaccharides include combinations of two monosaccharide, suitably pyranoses, linked by a glycosidic bond, for example rhamnose and glucose, for example L-rhamnose and D-glucose.

Suitable disaccharides can have the structure:

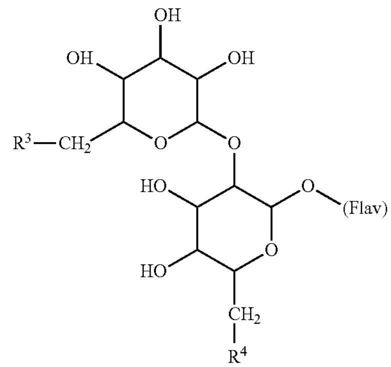

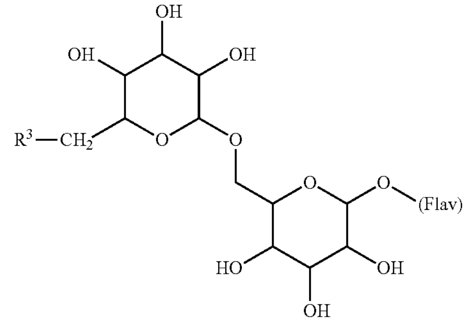

wherein one of $R^3$ and $R^4$ is H and the other OH or both are H or both are OH. Aptly $R^3$ is H and $R^4$ is OH so that the disaccharide is rutinose.

Favoured aglycones of flavonoids for use in this invention are the disaccharides 6-O-(alpha-L-rhamnopyranosyl)-beta-D-glucopyranose, also known as rutinose, and 2-O-(alpha-L-rhamnopyra-nosyl)-beta-D-glucopyra-rose.

DETAILED DESCRIPTION OF THE INVENTION

It is presently believed that the flavonoids very suitably comprise naringin or neohesperidin or mixtures thereof. Mixtures of one or both of naringin and neohesperidin with for example, one, two or three other flavonoids of the Formula I are presently believed particularly favoured for use in this invention. Such mixtures can be obtained from extraction from bitter oranges.

Suitable compounds of Formula (I) include Neoeriocitrin, Isonaringin, Naringin, Hesperidin, Neohesperidin, Neodiosmin, Naringenin, Poncirin and Rhiofolin.

Favoured compositions for use include those which comprise either of naringin and neohesperidin or both.

Particularly aptly the invention will contain naringin and neohesperidin and other flavonoids of the Formula (I).

The mixture of flavonoids may aptly contain more than one of neohesperidin, naringin, isocriocrin, isonaringin, naringin, hesperidine, neohesperidin, neocliomin, naringenin, poncrin and rhiofolin. Such a mixture of flavonoids can be obtained from bitter oranges, see for example PCT/GB2007/002756. Suitable mixtures can include 2, 3, 4, 5, 6, 7, 8, 9 or more compounds of Formula (I). Thus a mixture comprising 2, 3, 5, 6, 7, 8 or 9 of the above named flavonoids is apt, for example containing 3, or containing 4, or containing 5, or containing 6, or containing 7, or containing 8 or containing 9 of said flavonoids.

It is presently believed that mixtures of such flavonoids have advantages over the use of a single flavonoid. It is particularly advantageous that extract of bitter oranges may be employed without the need for isolating individual flavonoids if desired. The use of the composition generally comprising biomass enhances solubility of the flavonoids. Generally the flavonoids are present in mixtures with biomass by about 10% to 75%, more aptly 30% to 60%, for example 40% to 50%, preferably about 45%. The biomass comprises pectins and other sugar derived materials. Typically about 40% of low molecular weight pectins are present.

If it is desired to avoid biomass, other solubilising agents such as dextrins, for example cyclodextrin, may be employed if desired.

Aptly the mixture of flavonoids will comprise at least 25%, more suitably at least 40% and preferably at least 50% of naringin. More aptly the mixture will contain up to 65% of naringin.

Aptly the mixture of flavonoids will comprise at least 15%, more suitably at least 20% and preferably at least 25% of neohesperidin. More aptly the mixture will contain up to 35% of neohesperidin.

In a favoured form the mixture will contain at least 75% of neohesperidin and naringin.

A particular advantage of many compositions of the invention is that they may employ compounds of natural origin. Thus, for example, it is preferred to employ compounds of the Formula (I).

The use of these compositions does not require long periods where noxious gases can dissipate before the area can be utilized again. Similarly the sterilised area does not possess an appeasement order for long periods after sterilisation.

Compositions of the invention may be adapted for application to external surfaces including external surfaces of plants or animals. Often the animal is a human. Human clothing may also be misted to reduce the burden of unwanted organisms.

The compositions of the flavonoids show activity against a wide range of organisms including gram positive bacteria, gram negative bacteria, fungi, virus, protozoans and insect parasites when misted. Particularly surprising the misting may be employed against difficult bacteria such as methicillin resistant *staphylococcus aureus* (MRSA), *clostridium difficile* (C. diff) *helicobacter pylori* (H. py), and vancomycin resistant *enterobacteria*.

The compositions may be used to mist animals. Suitable animals include humans and food and companion animals such as cows, pigs, horses, chickens, sheep, goats, dogs and cats.

Suitable compositions for misting include those analogous to those described in PCT/GB2007/002756 and PCT/GB2007/002758.

These compositions may be in the form of solutions, dusting powders and other aerially dispersible powder and liquids and the like. Liquid forms are presently preferred. The use of "dry" mists of aqueous solutions can also be favourable.

UK Patent Application No 2450536 discloses misting devices that may be employed to mist solutions of the flavonoids described herein. This can be in the form of droplets of 0.5 to 5μ, for example about 1μ. These give the dry feel to the dispersion. Solutions of 0.5 to 7.5%, more aptly 1 to 5%, for example 1, 2, 3, 4 or 5% of HPLC-45 (see Example 1), or other flavonoid compositions described herein may be employed for dispersal.

Such compositions may be used to reduce the bacterial count on body surfaces, clothing and in the general environment particularly in hospitals, ambulances, nursing homes especially for the elderly or the like where it is particularly desirable to reduce the presence of bacteria such as MRSA, *C. difficile* or the like.

The compositions may be similarly employed in the home, for example in the kitchen, bathroom or toilet.

Small wall mounted misters may be employed in the domestic situation and also in hospital rooms and wards.

Such compositions may also be employed to mist equipment such as stethoscopes and other medical equipment.

A particular use of the composition is to mist hospital and other mattresses. This may play a role in reducing the transmission of *staphylococcus* including MRSA.

The substantivity of the compositions following misting (as opposed to rapid diminution of effectiveness of ethanol) is an advantage.

If external surfaces of enclosed spaces, such as ambulances, operating theatres, wards, kitchens (and even mortuaries) and so on are to be treated, it is particularly suitable to do so by "misting". In this a fine aerial dispersion of powder or microdroplets of composition are dispersed within the enclosed space. This can then offer a non-toxic alternative to the presently employed methods which often employ noxious gases. Since the compositions of the invention have such low toxicity they may be employed on patients and their visitors and associated clothing, linen and the like by "misting". Such "misting" is of use in vehicles such as ambulances which are required to be free of pathogens or at least have them reduced to an acceptable level, but likewise free of residual odors that are typically left following the use of noxious gases. This equally applies to other areas requiring treatment. Compositions used in this way may be in the form of a dispersible liquid, for example akin to the soap or shampoo or skin foaming compositions described hereinafter.

Thus it is possible by misting compositions of this invention to treat hands, the face and skin generally and the hair, both on the head and elsewhere. This can be employed to reduce bacterial count and so help to reduce the spread of methicillin resistant *staphylococcus aureas, clostridium difficile* and other bacteria. Similarly, misting clothing, hospital bedding and mattresses and the like can have a similar beneficial result. A further benefit is that such compositions may be used to reduce viral transmission, for example for influenza virus, which can occur by hand contamination. Other virus that may be on the skin or membranes include HIV, herpes and the like which are also minimized by use of the compositions of the invention adapted for administration to the skin or membranes. The use of this invention in treating environments which may contain multiple resistant vancomycin enterococci or spore forming organisms such as *clostridium difficile* may be advantageous.

External Parasite infestation may be treated by misting with compositions of the invention. External parasites that may be treated by misting include lice, especially head lice, and scabies and fleas.

Compositions of the invention may therefore also suitably contain a pharmaceutically acceptable salt of choline such as choline chloride. This can enhance effectiveness further against organisms such as *c. difficile*.

Formulations may be composed of conventional carriers as long as they are compatible with the active components of the compositions herein.

The mistable composition may aptly contain surfactants. Many conventional surfactants may be employed but it appears certain effective formulations will employ non-ionic surfactants. Particularly effective non-ionic surfactants include alkyl polycyclosides and/or alkenyl polyglycosides (APG's) such as those containing up to 10 sugar residues coupled to a hydrocarbon chain. Oligomerisation of up to about 4 sugar residues can be desirable. Such surfactants are available under the trade name "Plantacare" for example from Henkel as "Plantacare 2000".

In some compositions minor amounts of typical anionic surfactants may be employed together with the non-ionic surfactant. Amphoteric surfactants may also be present with the non-ionic surfactants, for example those having secondary or tertiary amino and water solubilising anionic groups, such as sulphate, phosphate, phosphonate or carboxylate groups. Such amphoteric surfactants include those available under trade names such as Miranol (of Rhone-Poulenc) and Betain, such as Dehyton from Henkel.

The compositions of the invention may optionally comprise thickening agents. Suitable thickening agents include polysaccharide thickeners such as xanthan gums, gellan gums, pectins, carrageenans and the like. An apt thickening agent is xanthan gum such as Keltrol CG which is a high molecular weight polysaccharide produced by microbial fermentation. Viscosity may also be selected by use of an amphoteric surfactant such as a cocamido-propyl betain or Tego Betain F50 as a thickening as well as surfactant agent.

Misting may be performed in gyms, changing rooms, schools, public transport and other areas where it is particularly advantageous to employ non-noxious sterilizing systems.

The use in such areas can have the added benefit of deodorizing the areas.

The compositions of the invention may be misted for the treatment of food stuffs to reduce or eliminate unwanted pathogens or organisms leading to reduction in storage life of food stuffs. Thus vegetable, fruits and meat may be treated, for example lettuce, tomatoes, cucumbers, peppers, cereals such as wheat and maize, fruit such as apples, grapes, pears and figs, and meats such as beef, pork, lamb, bacon and the like.

The skilled person understands that "sterilizing" in the context of this document may have the normally recognized meaning to the skilled person of reducing or eliminating unwanted pathogens or organisms in the relevant environment to a level where the environment is then more fit for purpose, for example not presenting a health risk.

EXAMPLE 1

Water was added to a beaker and stirring commenced. Keltrol CG-SFT (9.0 g; 1.8%) was added and stirring continued until dissolved. Citrox HXT powder (2.5 g; 0.5%) was added and stirring continued until dissolved. Glycerol (5.0 g; 1.0%) was added and stirring continued until dissolved. (The water was sufficient to make up to 100%).

The resulting viscous gel was de-aerated. The pH was 4-5. The viscosity 7000-10000 cp at 20° C. (spindle 4/0 rpm). The pH may be adjusted with citric acid if required to bring it within the stated range.

Citrox HXT powder comprises on a wt/wt basis 7.5% HPLC 45%, citric acid 30%, willow bark extract 50% and *olea Europeae* extract 12.5%.

HPLC-45% contained 45% by weight of a mixed of flavonoids together with residues of extraction from bitter oranges.

The mixture of flavonoids in HPLC-45 comprises:

| Bioflavonoid | % in HPLC 45 (bioflavonoid component + biomass) |
| --- | --- |
| Neoeriocitrin | 1.1 |
| Isonaringin | 1.2 |
| Naringin | 23.4 |
| Hesperidin | 1.4 |
| Neohesperidin | 12.5 |
| Neodiosmin | 1.4 |
| Naringenin | 1.5 |
| Poncirin | 2.0 |
| Other | 0.5 |
| (Rhiofolin) | |
| Total | 45% of HPLC 45 |

EXAMPLE 2

Water was added to a beaker and stirring commenced. Keltrol CG-SFT (9 g, 1.8%), Plantacare 2000 (67.8 g, 13.6%), Tego Betain F50 (10 g, 2%), glycerol (10 g, 2%) and Citrox HXT powder were sequentially added with stirring until complete dissolution occurred prior to adding subsequent ingredients. (The water was sufficient to make up to 100%).

The product was a clear viscous gel, pH 4.8 to 5 was a viscosity of about 4000 cp at 20° C. (spindle 4/10 rpm).

Citrox HXT powder and Keltrol CG-SFT were as described in Example 1.

Plantacare 2000 is an aqueous solution containing 6.78 g of $C_8$-$C_{16}$ fatty alcohol polyglycoside.

Tego Betain F50 is an aqueous solution containing 3.22 g of cocamidopropyl betaine.

EXAMPLE 3

This was prepared by mixing as described in Example 1.

| | |
| --- | --- |
| Salicylic acid | 0.25% |
| Citric acid | 0.15% |
| HPLC 45% | 0.0375% |
| Betafin BP20 | 1.0% |
| Glycerine | 0.5% |
| Dermosoft GMCY | 1.0% |
| Water | 97.0% |

EXAMPLE 4

This was prepared by mixing as described in Example 1.

| | |
| --- | --- |
| Keltrol CG-SFT | 1.7% |
| HPLC 45% | 0.0375% |
| Citric acid | 0.15% |
| Salicylic acid | 0.25% |
| Dermosoft GMCY | 1.0% |
| Glycerine | 1.0% |
| Water | 95.8% |

EXAMPLE 5

| | |
|---|---|
| Keltrol CG-SFT | 1.8% |
| Plantacare 2000 | 13.56% |
| Tego Betain F50 | 9.48% |
| Glycerine | 1.0% |
| HPLC 45% | 0.0375% |
| Citric acid | 0.15% |
| Salicylic acid | 0.25% |
| Dermosoft GMCY | 1.0% |
| Water | 72.66% |

When used herein HPLC 45% means a mixture containing 45% of bioflavonoids and 55% of other matter from extraction of bitter oranges. The bioflavonoids comprised naringin (about 52%), neohesperidin 28%, poncirin (4%), naringenin (3%), hesperidin (3%), neodiosmin (3%), isonaringin (3%), isocriocrin (2%), other minor to 100%.

EXAMPLE 6

Example 5 is repeated by adding choline chloride (1.25 g; 0.25%) after the keltrol and stirring until dissolved.

EXAMPLE 7

Compositions formulated as exemplified in PCT/GB2007/002756 and PCT/GB2007/002758 are misted from a misting device.

EXAMPLE 8

Compositions 1 to 6 are misted from a misting device.

A commercial hand held misting device is used to direct mist at the surfaces in an ambulance and to the air space. The misting is continued until the operative is satisfied surfaces have been thoroughly treated.

The ambulance may be occupied twenty minutes after the completion of the misting.

EXAMPLE 9

A composition described in Example 1 was used to mist a microbiological research laboratory to reduce biological contamination. The misting was performed for three hours. If entry to the laboratory had become necessary, this would have been possible owing to the lack of significant toxicity of the mist. A conventional commercial misting device was employed.

The Nebulair was turned on each night for three hours in a sealed room over a 16 day period. A 1% aqueous solution of HPLC-45 as described in Example 1 was used between day 1 and 7 and was then increased to a 2% aqueous solution. An area of 100 cm² was swabbed using a saturated swab and added to a sterile tube containing 3 ml maximum recovery diluent (MRD). The tubes were vortexed for 20 seconds and then left to stand for 20 minutes. The swabs were removed and 100 µl (Day 0 and Day 1) or 200 µl (Day 3, 9, 11, and 16) of MRD was spread on TSB agar plates. A clean swap was used as a control. The plates were incubated at 37° C. for 24 hours and the average number of colonies per plate was recorded.

Results:

| | Colony Forming Units (CFU) per 100 cm² | | | | | |
|---|---|---|---|---|---|---|
| | Day 0 | Day 1 | Day 3 | Day 9 | Day 11 | Day 16 |
| Computer | 3600 | 435 | 195 | 285 | 97.5 | 90 |
| Desk 1 | 600 | 45 | 15 | 15 | 7.5 | 0 |
| Desk 2 | 60 | 0 | 15 | 7.5 | 15 | 7.5 |
| Desk 3 | 150 | 45 | 75 | 7.5 | 7.5 | 0 |
| Desk 4 | 150 | 15 | 15 | 7.5 | 7.5 | 0 |
| Under Desk | 150 | 15 | 30 | 0 | 0 | 0 |
| Bin | 510 | 240 | 45 | 22.5 | 22.5 | 15 |
| Sink | 1890 | 570 | 172.5 | 82.5 | 210 | 127.5 |
| Centrifuge | 210 | 45 | 90 | 37.5 | 15 | 0 |
| Extractor fan | 255 | 225 | 15 | 45 | 15 | 15 |
| Water Bath | 660 | 90 | 30 | 22.5 | 22.5 | 7.5 |

Note:
Bioflavanoid mixture concentration increased from 1% to 2% after day 7 Day 0 indicates contamination levels before misting treatment

EXAMPLE 10

The surface of a hospital mattress was misted with either 3% or 5% aqueous solutions of HPLC-45 (see Example 1) for 3 hours from a commercial dry misting nebuliser (Nebulair). The misting in both cases was effective in reducing the presence of multiple resistant *staphylococcus aureus* to a greater extent than was achieved by the hospitals conventional treatment.

The invention claimed is:

1. A method of sterilizing surfaces of fruit comprising forming a fine aerial dispersion of powder which are non-toxic to humans and which contact said surface of the fruit and wherein the powder contain an effective amount of a mixture of bioflavonoids which comprise 40% to 65% of naringin and 20% to 35% neohesperidin.

2. The method as claimed in claim 1 wherein the mixture comprises at least 75% of neohesperidine and naringin.

3. The method as claimed in claim 1 wherein misting is employed to aid prevention of spread of methicillin resistant *staphylococcus aureus*.

4. The method as claimed in claim 1 wherein misting is employed to aid prevention of spread of *clostridium difficile*.

5. The method as claimed in claim 1 wherein the composition further comprises a surfactant.

6. The method as claimed in claim 5 wherein the composition comprises a mixture of flavanoids together with residues of extraction from bitter oranges.

7. The method as claimed in claim 1 wherein the mixture of bioflavonoids comprises HPLC-45%.

8. The method as claimed in claim 1 wherein the surfaces are exposed to the composition for 2 minutes to 20 minutes.

9. The method as claimed in claim 1 free of noxious odours.

10. The method as claimed in claim 1 wherein the powder further comprises citric acid.

11. The method as claimed in claim 1 wherein the fruit is apples, grapes, pears, or figs.

* * * * *